United States Patent [19]

Oguri et al.

[11] Patent Number: 5,026,941
[45] Date of Patent: Jun. 25, 1991

[54] Y ZEOLITE CATALYST

[75] Inventors: Motohiro Oguri; Yoshiaki Kano; Kiyotaka Mishima; Masahiko Yamada, all of Yotsukaichi; Kenji Kasano, Mie; Masaru Uemura, Yotsukaichi, all of Japan

[73] Assignee: Tosho Corporation, Japan

[21] Appl. No.: 604,989

[22] Filed: Oct. 26, 1990

Related U.S. Application Data

[63] Continuation of Ser. No. 329,631, Mar. 28, 1989, abandoned.

[30] Foreign Application Priority Data

Mar. 28, 1988 [JP] Japan .................................. 63-73945
Mar. 28, 1988 [JP] Japan .................................. 63-73946

[51] Int. Cl.$^5$ .................................................. C07G 2/68
[52] U.S. Cl. .................................................. 585/467
[58] Field of Search ......................................... 585/467

[56] References Cited

U.S. PATENT DOCUMENTS 3,897,327  7/1975  Ward .
4,026,959  5/1977  Kemme et al. .
4,836,911  6/1989  Skeels et al. .................. 585/467

FOREIGN PATENT DOCUMENTS 51-56435   5/1976  Japan .
54-122700  9/1979  Japan .
55-45533  11/1980  Japan .
62-226931 10/1987  Japan .

OTHER PUBLICATIONS

Forni et al. Ind. Eng. Chem. Res. 1987, 26, 1860–1864.

Primary Examiner—Curtis R. Davis
Attorney, Agent, or Firm—Jacobs & Jacobs

[57] ABSTRACT

A catalyst comprising a Y zeolite of which silica/alumina molar ratio ranges from 15 to 110, use of this catalyst for alkylation of monoisopropylnaphthalene and a method for preparation of this catalyst comprising treating a Y zeolite with an acid(s) to adjust the silica/alumina molar ratio to 15 to 110 are disclosed. A method for preparation of mono and/or diisopropylnaphthalenes comprising reacting naphthalene and/or monoisopropylnaphthalene with propylene in the presence of at least one saturated polycarbocyclic compounds and a catalyst comprising a Y zeolite having the silica/alumina molar ratio of from 10 to 350 are disclosed. This catalyst makes possible the production of $\beta$-monoisopropylnaphthalene in good yield by alkylation of naphthalene and the production of $\beta$-monoisopropylnaphthalene and/or 2,6- and 2,7-diisopropylnaphthalenes in good yield by alkylation of naphthalene and/or monoisopropylnaphthalene in good percent conversion.

14 Claims, 2 Drawing Sheets

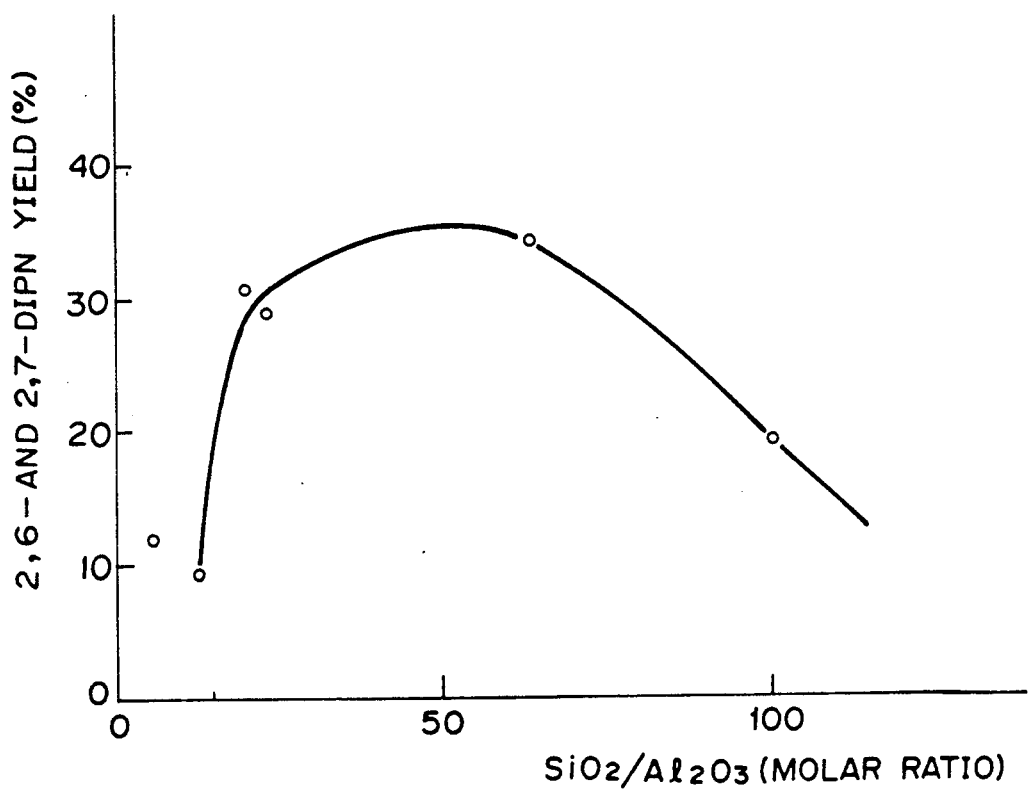
F I G .1

5,026,941

Y ZEOLITE CATALYST

This is a continuation of application Ser. No. 07/329,631, filed Mar. 28, 1989 and now abandoned.

BACKGROUND OF THE INVENTION

1. Field of the Invention

The present invention relates to a novel Y zeolite catalyst, a method for preparation thereof and a method for preparation of monoisopropylnaphthalene and/or diisopropylnaphthalene using this Y zeolite catalyst. Particularly, the present invention relates to a catalyst containing a specific Y zeolite, and this catalyst makes possible the production of $\beta$-monoisopropylnaphthalene in high yield by alkylation of naphthalene and the production of $\beta$-monoisopropylnaphthalene and/or 2,6- and 2,7-diisopropylnaphthalenes in good yield by alkylation of naphthalene and/or monoisopropylnaphthalene in good percent conversion.

2. Description of the Prior Art 2,6- and 2,7-diisopropylnaphthalenes are useful as intermediates for preparation of polymers. Among them, 2,6-diisopropylnaphthalene can be utilized widely because 2,6-naphthalenedicarboxylic acid obtained by its oxidation is used as starting materials for synthesis of polyester (synthetic fiber and film).

A method for preparation of diisopropylnaphthalenes comprising alkylating naphthalene with propylene in the presence of Lewis acids such as $AlCl_3$ to obtain monoisopropylnaphthalene and/or 2,6-and 2,7-diisopropylnaphthalenes is well-known. However, in this alkylation method, reaction products have to be separated from the catalyst after completion of the reaction. Further this method is not economical since the catalyst used has properties corroding a reaction apparatus.

Japanese Patent Disclosure (KOKAI) No. 51-56435 discloses a process for preparing isopropylnaphthalene comprising alkylation of naphthalene with propylene using a $BF_3$—$H_3PO_4$ adduct catalyst instead of $AlCl_3$.

However, the $BF_3$—$H_3PO_4$ adduct catalyst has the same corrosive properties as $AlCl_3$ has. Further, after completion of the reaction, isomerization of the resulting reaction products is necessitated because of the low selectivity of objective $\beta$-monoisopropylnaphthalene.

On the other hand, Japanese Patent Publication (KOKOKU) No. 55-45533 discloses a method for preparation of $\beta$-monoisopropylnaphthalene using a solid catalyst easily separable from reaction products, in which naphthalene is alkylated with propylene using an aluminum oxyhalide or a titanium oxyhalide as the catalyst. However, a large amount of high boiling point substances are produced and $\beta$-monoisopropylnaphthalene content based on total monoisopropylnaphthalene is low.

U.S. Pat. No. 4,026,959 discloses a process for increasing $\beta$-monoisopropylnaphthalene content comprising isomerization of a mixture of isopropylnaphthalenes using a rare earth metal ammonium ion-exchanged Y zeolite.

Furthermore, Japanese Patent Disclosure No. 62-226931 discloses a process for preparation of diisopropylnaphthalene comprising alkylating naphthalene with propylene using silica-alumina or synthetic mordenite as the catalyst. However, the reaction temperature of this process is high (250°–350° C.) and the resulting diisopropylnaphthalene containing products have to be concentrated by repeating precision distillations in order to recover 2,6-diisopropylnaphthalene by crystalization since the content of 2,6-diisopropylnaphthalene in the products is low.

A method for alkylation of naphthalene and/or monoisopropylnaphthalene in good percent conversion by using a solid catalyst having a long activity life, particularly a method for preparing monoisopropylnaphthalene in good selectivity of $\beta$-monoisopropylnaphthalene (high $\beta$-isomer content) and a method for preparing 2,6- and 2,7-diisopropylnaphthalenes in good selectivity have not yet been established. Accordingly, an object of the present invention is to provide a catalyst useful for a method for preparation of mono and/or diisopropylnaphthalenes having a long activity life.

Another object of the present invention is to provide a method for preparation of mono and/or diisopropylnaphthalenes of which percent conversion of starting materials such as naphthalene and selectivity of $\beta$-monoisopropylnaphthalene and 2,6- and 2,7-diisopropylnaphthalenes are good.

Further object of the present invention is to provide a catalyst capable of converting monoisopropylnaphthalene into 2,6-diisopropylnaphthalene in good selectivity.

Furthermore object of the present invention is to provide a catalyst capable of converting monoisopropylnaphthalene into 2,7-diisopropylnaphthalene in good selectivity in addition to 2,6-diisopropylnaphthalene.

The other object of the present invention is to provide a catalyst for preparation of diisopropylnaphthalene with a long activity life.

SUMMARY OF THE INVENITON

The present invention relates to a catalyst for preparation of diisopropylnaphthalene comprising Y zeolite of which molar ratio of silica to alumina ranges from 15 to 110.

BRIEF EXPLANATION OF DRAWINGS

FIG. 1 shows the relationship between the silica/alumina molar ratio of the Y zeolite catalyst and yield of 2,6- and 2,7-diisopropylnaphthalenes.

DESCRIPTION OF THE INVENTION

Figure 2:
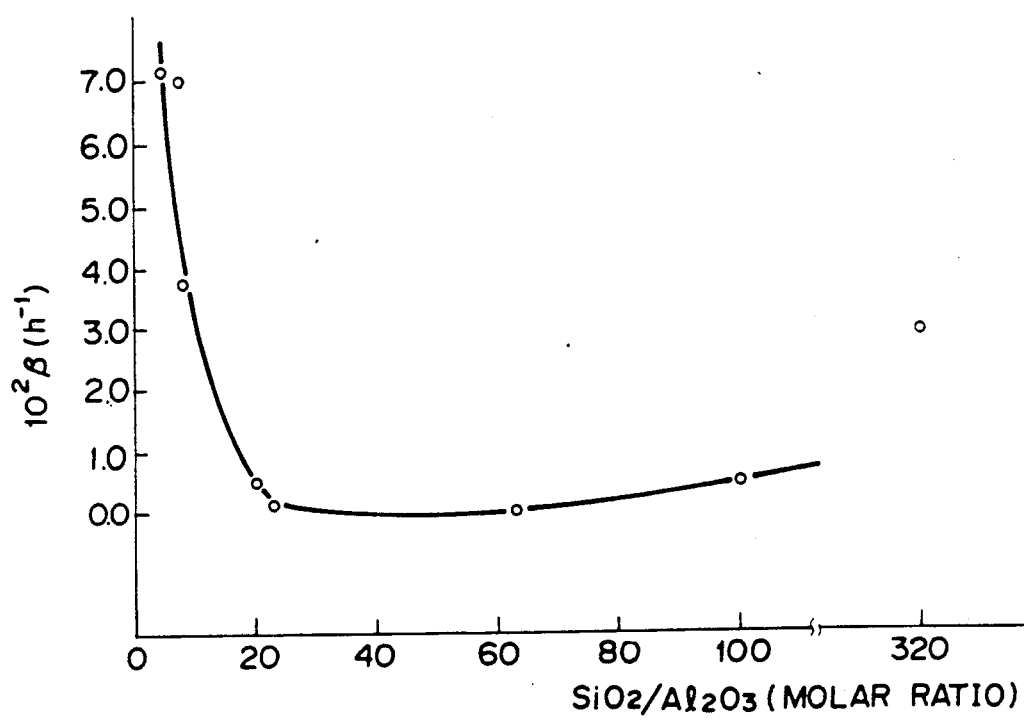
FIG. 2 shows the relationship between the silica/alumina molar ratio of the Y zeolite catalyst and an activity life of the catalyst.

The present invention will now be explained in detailed.

The catalyst of the present invention can be prepared by treating a Y zeolite with an acid(s) to adjust the silica/alumina molar ratio within 15 to 110.

Y zeolites are used as starting materials of the catalyst used in this invention. There is no limitation on a preparation method thereof and any Y zeolites can be used for this purpose. However, from the viewpoint of inhibiting destruction of crystals at subsequent acid treatment, it is preferred to use a Y zeolite with good stability of the crystal structure (hereinafter referred to as an ultrastable Y zeolite).

Cation sites of zeolites are generally occupied with alkali metals such as sodium and these metals are substituted with hydrogen ions before reaction. Similarly, a Y zeolite is subjected to ion-exchaging and it is well-known that its hydrothermal stability is improved by heat treating in the presence of steam or treating with dilute mineral acids to reduce $Na_2O$ content to 1% by weight or less. The ultrastable Y zeolite can be prepared by the methods disclosed in, for example, Japanese Patent Disclosure Nos. 54-122700 and 56-22624. One of examples thereof will be shown below.

Starting Y zeolite containing Na is treated with an aqueous ammonium salt(s) solution so as to ion-exchange 50 to 75% of Na with ammonium. Examples of ammonium salts(s) used include chlorides, nitrates, sulfates, carbonates and acetates, particularly chlorides and sulfates are preferred. When sodium ions are not exchanged with ammonium ions up to 50 to 75% by a single ion-exchanging treatment, the similar treatment can be repeated once more.

The resulting Y zeolite of which 50 to 75% of Na have been ion-exchanged with ammonium ions is then subjected to calcination at a high temperature (for instance, 400° to 900° C.) in the presence of steam for from 10 minutes to 5 hours. This calcined Y zeolite is again treated with an aqueous ammonium salt(s) solution followed by heat treatment at a high temperature (for instance, 400° to 900° C.) in the presence of steam for from 10 minutes to 5 hours to obtain HY zeolite of which stability of crystal structure is improved. Alternatively, the stability of the crystal structure can be improved by treatment of the calcined Y zeolite with a dilute mineral acid solution in several times. In this case, a concentration of the mineral acid is adjusted by controlling the pH value of the solution within 1.0 to 5.0 in order to inhibit destruction of the crystal structure.

In this invention, Y zeolite is treated with an acid(s) (inorganic acid and/or organic acid) to dealuminate. An increase of the silica/alumina molar ratio after the dealumination varies depending on a hydrogen ion concentration upon dealumination, treating temperature and treating time. Among them, the effect of the hydrogen ion concentration is the greatest and it is preferred to adjust the hydrogen ion concentration by controlling the pH value within 0.01 to 4.0. When the pH value of the treating solution is controlled within 0.01 to 4.0, it is suitable that the treating temperature ranges from 10° to 200° C. and the treating time ranges from 30 minutes to 30 hours. As a manner of treatment, a batch method is preferred and the solid-liquid ratio is preferably 1 to 30.

Both of inorganic acids and organic acids can be used as the acid used for dealumination. Examples of the inorganic acids include hydrochloric acid, sulfuric acid, nitric acid and phosphoric acid. Examples of the organic acids include carboxylic acids and sulfonic acids. Particularly, super-strong acids such as trifluoromethanesulfonic acid can be used as the organic acids.

When the silica/alumina molar ratio of the treated Y zeolite does not reach the prescribed level by a single treatment, the same treatment as that described above can be repeated once or more.

The dealuminated Y zeolite is washed with ion-exchanged water sufficiently and then calcined at a high temperature (for example 400° to 600° C.) for from 2 to 6 hours to obtain the catalyst of the present invention.

The silica/alumina molar ratio of the catalyst of the present invention preferably ranges from 15 to 110. The catalyst having the ratio within this range enables a remarkable improvement of yield (percent conversion × selectivity) of 2,6- and 2,7-diisopropylnaphthalenes as shown in FIG. 1. Further, by ranging the silica/alumina molar ratio within the above range, the Y zeolite catalyst converts starting materials in good percent conversion and the activity life of Y zeolite catalyst is remarkably improved.

The Y zeolite used in the present invention can be used in the form of powder. Alternatively, it can be used in the form of molding powder such as pellet or tablet obtained by compression molding. A binder such as alumina sol and silica sol can be used for the molding of the Y zeolite. Further, the Y zeolite can be molded after the dealumination.

Alkylation of monoisopropylnaphthalene by the method of the present invention can be conducted either in a gas phase or in a liquid phase and is preferably conducted in a liquid phase. The alkylation is preferably carried out under pressure and the reaction pressure may range from 0.5 to 100 kg/cm$^2$G, preferably 0.5 to 30 kg/cm$^2$G. The alkylation under pressure tends to increase an yield of objective diisopropylnaphthalenes because elimination of isopropyl groups is hard to occur. Provided that effects of the reaction pressure on the yield is substantially null at 30 kg/cm$^2$G or more.

The alkylation of the present invention is preferably carried out at a temperature of from 160° to 300° C. Within this temperature range, dealkylation reaction can be inhibited, the catalyst exhibits high activity and deterioration of the catalyst can be minimized.

The alkylation of the present invention is preferably conducted in a stream of hydrogen to maintain the catalyst activity for long time. Hydrogen is supplied preferably in the range of from 0.1 to 10 mol on the basis of 1 mol of monoisopropylnaphthalene. Further, other gases such as nitrogen, carbon dioxide and methane can be used in place of hydrogen or together with hydrogen. The alkylation reaction is generally carried out by using a reaction apparatus with a fixed bed and those having a fluidized bed or a moving bed also can be used. Weight hourly space velocity (WHSV) may ranges from 0.2 to 50 Hr$^{-1}$, preferably 1 to 20 Hr$^{-1}$. High productivity can be obtained at 1 or more of WHSV. WHSV of 50 Hr$^{-1}$ or less makes possible the contact of reacting substances with the catalyst for sufficiently long time and results in good percent conversion. WHSV means herein an amount (g) of naphthalene and/or monoisopropylnaphthalene supplied to 1 g of the catalyst for one hour.

An amount of propylene supplied to the alkylation of the present invention suitably ranges from 0.2 to 2.0 mol (on the basis of 1 mol of monoisopropylnaphthalene), preferably 0.3 to 1.5.

Diisopropylnaphthalenes can be prepared from monoisopropylnaphthalene in good percent conversion by using the catalyst of the present invention. Further the catalyst of the present invention has an improved activity life.

The content of 2,6- and 2,7-diisopropylnaphthalenes, which are useful isomers among the mixture of diisopropylnaphthalene isomers obtained by using the catalyst of the present invention, is remarkably high. Thus highly pure 2,6-diisopropylnaphthalene can be recovered as crystals by crystallizing a diisopropylnaphthalenes fraction obtained by distillation without any further concentration.

The above mentioned characters of the present invention are advantageous for industrial use.

Other aspects of the present invention will be explained in detail.

The present invention relates to a process for preparation of mono and/or diisopropylnaphthalenes comprising reacting naphthalene and/or monoisopropylnaphthalene with propylene in the presence of at least one saturated polycarbocyclic compounds and a catalyst comprising Y zeolite having the silica/alumina molar ratio of from 10 to 350.

The catalyst used in the present invention can be prepared by treating a Y zeolite with an acid to adjust the silica/alumina molar ratio within 10 to 350. The treatment with the acid can be conducted by the same manner as that described above.

Forni et al reported that the activity life of catalysts can be represented easily by logarithm value ($\beta$ value) of deactivation against reaction time (refer to Industry and Engineering Chemistry Research, vol 26, p1860-1864 (1987)). The $\beta$ value is calculated by the following formula:

$$Y^t/Y^o = \exp(-\beta t)$$

$Y^t$: percent conversion at t hours from the begining of reaction $Y^o$: percent conversion at the begining of reaction A smaller value of $\beta$ denotes a smaller deactivation of catalytic activity. The relationship between the silica/alumina molar ratio of the Y zeolite used in the present invention and the $\beta$ value representing its life is shown in FIG. 2. As seen from FIG. 2, the preferred catalyst used in the present invention has the silica/alumina molar ratio in the range of from 10 to 350. That is, by using the Y zeolite with the silica/alumina molar ratio of 10 to 350, the $\beta$ value can be minimized to one-half or less that of an un-treated catalyst.

Y zeolites used in the present invention can be used in the form of powder. Alternatively, it can be used in the form of molding powder such as pellet or tablet obtained by the compression molding. A binder such as alumina sol and silica sol can be used for the molding of Y type zeolite. Further, Y zeolite can be molded after the dealumination.

Examples of saturated polycarbocyclic compounds used in the present invention include polycarbocyclic compounds with separate ring-systems, polycarbocyclic compounds with combined ring-systems, polycarbocyclic compounds with fused ring-systems and polycarbocyclic compounds with bridged ring-systems. Examples of the polycarbocyclic compounds with separate ring-systems include bicyclopropyl, bicyclopentyl, bicyclohexyl and cyclopentylcyclohexane. Examples of the polycarbocyclic compounds with combined ring-systems include so-call spirane compounds such as spiro[2,2]heptane, spiro[2,3]hexane, spiro[2,4]heptane, spiro[3,3]heptane and spiro[3,4]octane. Examples of the polycarbocyclic compounds with fused ring-systems include bicyclo[4,2,0]octanehydroindane, decalin (decahydronaphthalene), perhydrophenanthroline and perhydroanthracene. Examples of the polycarbocyclic compounds with bridged ring-systems include norpinane, norbornane, bicyclo[2,2,1]octane. Among these, the polycarbocyclic compounds with fused ring-systems and polycarbocyclic compounds with separate ring-systems are preferred and particularly decalin and bicyclohexyl are preferred. Both of decalins, cis-decalin and trans-decalin are preferably used and a mixture thereof are preferred because it is easily available.

An amount of the saturated polycarbocyclic compounds supplied to the reaction preferably ranges from 0.01 to 20 (weight ratio against the weight of naphthalene and/or monoisopropylnaphthalene). The deterioration of activity is inhibited and the starting materials are converted in good percent conversion by adjusting the supply amount to the above range.

The saturated polycarbocyclic compounds can be supplied to the reaction either alone or together with naphthalene and/or monoisopropylnaphthalene.

Alkylation of naphthalene and/or monoisopropylnaphthalene with propylene by the method of the present invention can be conducted either in a gas phase or in a liquid phase and preferably conducted in a liquid phase. The alkylation is preferably carried out under pressure and the reaction pressure may range from 0.5 to 100 kg/cm$^2$G, preferably 0.5 to 30 kg/cm$^2$G. The alkylation under pressure tends to increase an yield of objective mono and/or diisopropylnaphthalenes because elimination of isopropyl groups is hard to occur. Provided that effects of the reaction pressure on the yield is substantially null at 30 kg/cm$^2$G or more.

The alkylation of the present invention is preferably carried out at a temperature of from 160° to 300° C. Within this temperature range, dealkylation reaction can be inhibited, the catalyst exhibits high activity and deterioration of the catalyst can be minimized.

The alkylation of the present invention is preferably conducted in a stream of hydrogen to maintain the catalyst activity for long time. Hydrogen is supplied preferably in the range of from 0.1 to 10 mol on the basis of 1 mol of naphthalene and/or monoisopropylnaphthalene. Further, other gases such as nitrogen, carbon dioxide and methane can be used in place of hydrogen or together with hydrogen. The alkylation reaction is generally carried out by using a reaction apparatus with a fixed bed and those having a fluidized bed or a moving bed also can be used. Weight hourly space velocity (WHSV) may ranges from 0.2 to 50 Hr$^{-1}$, preferably 1 to 20 Hr$^{-1}$. High productivity can be obtained at 1 or more of WHSV. WHSV of 50 Hr$^{-1}$ or less makes possible the contact of reacting substances with the catalyst for sufficiently long time and results in good percent conversion. WHSV means herein an amount (g) of naphthalene and/or monoisopropylnaphthalene supplying to 1 g of the catalyst for one hour.

An amount of propylene supplied to the alkylation of the present invention suitably ranges from 0.2 to 2.0 mol (on the basis of 1 mol of naphthalene and/or monoisopropylnaphthalene), preferably 0.3 to 1.5.

Diisopropylnaphthalenes can be prepared from monoisopropylnaphthalene in good percent conversion by using the catalyst of the present invention. Further the catalyst of the present invention has an improved activity life.

According to the present invention comprising reaction of naphthalene and/or monoisopropylnaphthalene with proplylene in the presence of at least one saturated polycarbocyclic compounds and a catalyst comprising Y zeolite having the silica/alumina molar ratio of from 10 to 350, the starting materials are converted in good percent conversion. Further, the catalyst has a long activity life.

The content of $\beta$-isopropylnaphthalene in the mixture of monoisopropylnaphthalene isomers is high and therefore any further isomerization is not necessary. Further, the content of 2,6- and 2,7-diisopropylnaphthalenes, which are useful isomers among the mixture of diisopropylnaphthalene isomers obtained by using the catalyst of the present invention, is remarkably high. Thus highly pure 2,6-diisopropylnaphthalene can be recovered as crystals by crystallizing a diisopropylnaphthalenes fraction obtained by distillation without any further concentration.

The above mentioned characters of the present invention are advantageous for industrial use.

EXAMPLE

The present invention will now be explained more in detail with reference to Examples but the present invention is not limited to the Examples.

EXAMPLE 1

20 g of an ultrastable Y zeolite improved in its hydrothermal stability (manufactured and sold by TOSOH Co. Ltd., TSZ-330HUA), which has 5.9 of the silica/alumina molar ratio and contains 0.21% by weight of $Na_2O$, was dispersed in 200 ml of an aqueous hydrochloric acid solution (0.80 mol/l) and this dispersion was stirred at 95° C. for two hours. After separation by a filter, the residue was sufficiently washed with water. The resulting zeolite was dried for one day and calcined at 500° C. for 5 hours to obtain a catalyst (hereinafter referred to as USY-1). According to an X-ray diffraction pattern, the lattice constant of the resulting zeolite slightly decreased, that is, the lattice constant was reduced to 24.24 Å from 24.41 Å of the ultrastable Y zeolite (starting material). Further, the silica/slumina molar ratio of USY-1 was 20.6. USY-1 was compression molded and the molded sample was ground. The ground sample was seived to obtain USY-1 with 20 to 42 mesh. This USY-1 (2 g) was filled in a fixed bed reaction apparatus. The catalyst bed was maintained at 220° C. and 20 g/Hr of isopropylnaphthalene ($\beta$-isomer content: 93%) and propylene (propylene/isopropylnaphthalene molar ratio=1/1) were supplied to the catalyst bed at the reaction pressure of 4 $kg/cm^2$. At the same time, hydrogen (hydrogen/isopropylnaphthalene molar ratio=4/1) was supplied to the catalyst bed, too. The results are shown in Table 1 and FIG. 1.

EXAMPLE 2

An ultrastable Y zeolite (20 g) the same as that used in Example 1 was dealuminated with 200 ml of an aqueous trifluoromethanesulfonic acid solution (0.80 mol/l) at 100° C. Then the dealuminated zeolite was sufficiently washed with water followed by drying at 90° C. for one day and calcining at 500° C. for 5 hours to obtain a catalyst (USY-2). The silica/alumina molar ratio of USY-2 was 22.9. According to the procedures of Example 1 except that USY-2 was used in place of USY-1 as the catalyst, alkylation reaction was carried out. The results are shown in Table 1 and FIG. 1.

EXAMPLE 3

An ultrastable Y zeolite (20 g) the same as that used in Example 1 was dealuminated with 200 ml of an aqueous trifluoromethanesulfonic acid solution (0.50 mol/l) at 100° C., and further with 200 ml of a trifluoromethane sulfonic acid solution (0.50 mol/l) and 200 ml of a trifluoromethane sulfonic acid solution (0.20 mol/l) at 100° C. Then the dealuminated zeolite was sufficiently washed with water followed by drying at 90° C. for one day and calcining at 500° C. for 5 hours to obtain a catalyst (USY-3). The silica/alumina molar ratio of USY-2 was 63.3. According to the procedures of Example 1 except that USY-3 was used in place of USY-1 as the catalyst, alkylation reaction was carried out. The results are shown in Table 1 and FIG. 1.

COMPARATIVE EXAMPLE 1

The alkylation reaction was conducted by the same manner as that of Example 1 except that an untreated ultrastable Y zeolite (manufactured and sold by TOSOH Co. Ltd., TSZ-330HUA) was used in place of USY-1 as the catalyst. The results are shown in Table 1 and FIG. 1. Deactivation of the catalyst was remarkable.

COMPARATIVE EXAMPLE 2

A dealuminated zeolite (USY-5) was obtained by the same manner as that of Example 1 except that an aqueous trifluoromethanesulfonic acid solution (0.40 mol/l) was used instead of the aqueous trifluoromethanesulfonic acid solution (0.80 mol/l). The silica/alumina molar ratio of USY-5 was 13.0. According to the procedures of Example 1 except that USY-5 was used in place of USY-1 as the catalyst, alkylation reaction was carried out. The results are shown in Table 1 and FIG. 1.

TABLE 1

| | Example 1 | | Example 2 | | Example 3 | | Example 4 | | Comparative example 1 | | Comparative example 2 | |
|---|---|---|---|---|---|---|---|---|---|---|---|---|
| Reaction conditions | | | | | | | | | | | | |
| Catalyst | USY-1 | | USY-2 | | USY-3 | | USY-4 | | TSZ-330 | | USY-5 | |
| $SiO_2/Al_2O_3$ | 20.6 | | 22.9 | | 63.3 | | 100 | | 5.9 | | 13.0 | |
| Temperature (°C.) | 220 | | 220 | | 220 | | 220 | | 220 | | 220 | |
| Pressure ($kg/cm^2G$) | 4.0 | | 4.0 | | 4.0 | | 4.0 | | 4.0 | | 4.0 | |
| Results | | | | | | | | | | | | |
| Reaction time (Hr) | 1 | 10 | 1 | 10 | 1 | 6 | 1 | 10 | 1 | 10 | 1 | 10 |
| IPN percent conversion (%) | 68.3 | 66.3 | 63.1 | 58.7 | 63.6 | 59.3 | 46.7 | 40.6 | 46.7 | 39.3 | 37.0 | 35.2 |
| NL selectivity (%) | 5.9 | 3.9 | 4.3 | 4.1 | 7.4 | 7.6 | 4.3 | 8.8 | 1.1 | 1.1 | 0.8 | 1.3 |
| DIPN selectivity (%) | 66.1 | 67.7 | 67.3 | 65.7 | 69.2 | 73.2 | 67.5 | 65.5 | 71.7 | 71.6 | 73.1 | 74.2 |
| TIPN selectivity (%) | 28.0 | 28.4 | 28.4 | 30.2 | 23.4 | 19.2 | 28.1 | 25.6 | 27.2 | 27.2 | 26.1 | 24.5 |
| DIPN isomers (%) | | | | | | | | | | | | |
| 2,6-DIPN | 41.5 | 38.2 | 39.3 | 38.1 | 41.0 | 42.1 | 40.3 | 36.4 | 23.1 | 23.6 | 22.6 | 22.6 |
| 2,7-DIPN | 38.2 | 32.5 | 34.2 | 31.9 | 37.6 | 36.8 | 29.1 | 27.6 | 15.8 | 16.2 | 14.6 | 14.6 |

TABLE 1-continued

|  | Example 1 | | Example 2 | | Example 3 | | Example 4 | | Comparative example 1 | Comparative example 2 |
|---|---|---|---|---|---|---|---|---|---|---|
| 2,6- and 2,7-DIPN yield (%) | 36.0 | 31.7 | 31.2 | 27.0 | 34.6 | 34.2 | 21.9 | 17.0 | 13.0  11.2 | 10.1  9.7 |

Remarks:
NL: naphthalene,
IPN: isopropylnaphthalene,
DIPN: diisopropylnaphthalene,
TIPN: tri or tetraisopropylnaphthalene
(1) IPN percent conversion: 100-IPN concentration (mol %) in products
(2) NL selectivity: [NL concentration (mol %) in products/IPN percent conversion (mol %)] × 100
(3) DIPN selectivity: [DIPN concentration (mol %) in products/IPN percent conversion (mol %)] × 100
(4) TIPN selectivity: [TIPN concentration (mol %) in products/IPN percent conversion (mol %)] × 100
(5) DIPN isomers: Concentration of 2,6- or 2,7-isomer in products of diisopropylnaphthalene isomers
(6) 2,6- and 2,7-DIPN yields: [2,6-DIPN selectivity + 2,7-DIPN selectivity] × DIPN selectivity × DIPN percent conversion / 100

EXAMPLE 5

USY-1 (20 to 42 mesh) (1 g) prepared in Example 1 was filled in a fixed bed reaction tube. The bed filled with USY-1 was maintained at 220° C. and 10 g/Hr of a mixing solution of isopropylnaphthalene (β-form content: 93%) and decalin (molar ratio 1/1), and propylene (propylene/isopropylnaphthalene molar ratio=1/1) were supplied to the bed at the reaction pressure of 4 kg/cm². At the same time, hydrogen (hydrogen/isopropylnaphthalene molar ratio=4/1) was supplied to the bed, too. The results are shown in Table 2 and FIG. 2.

EXAMPLE 6

An ultrastable Y zeolite the same as that used in Example 1 was dealuminated with 200 ml of an aqueous trifluoromethane sulfonic acid solution (0.50 mol/l) at 100° C. Then the dealuminated zeolite was sufficiently washed with water followed by drying at 90° C. for one day and calcining at 500° C. for 5 hours to obtain a catalyst (USY-6). The silica/alumina molar ratio of USY-6 was 14.9. According to the procedures of Example 5 except that USY-6 was used in place of USY-1 as the catalyst, alkylation reaction was carried out. The results are shown in Table 2 and FIG. 2.

EXAMPLE 7

A dealuminated zeolite (USY-7) was obtained by the same manner as that of Example 6 except that the dealumination was carried out by using 0.70 mol/l aqueous hydrochloric acid solution at 95° C. The silica/alumina molar ratio of USY-7 was 19.5. According to the procedures of Example 5 except that USY-7 was used in place of USY-1 as the catalyst, alkylation reaction was carried out. The results are shown in Table 2 and FIG. 2.

EXAMPLES 8 and 9

Alkylation reactions were conducted by the same manner as that of Example 5 except that USY-2 prepared in Example 2 (Example 8) or USY-3 prepared in Example 3 (Example 9) were used in place of USY-1 used in Example 5. The results are shown in Table 2 and FIG. 2.

EXAMPLE 10

An ultrastable Y zeolite the same as that used in Example 1 was dealuminated with 200 ml of an aqueous hydrochloric acid solution (0.50 mol/l) at 95° C., and further with 200 ml of an aqueous hydrochloric acid solution (0.50 mol/l) and 200 ml of an aqueous hydrochloric acid solution (0.20 mol/l) at 95° C. Then the dealuminated zeolite was sufficiently washed with water followed by drying at 90° C. for one day and calcining at 500° C. for 5 hours to obtain a catalyst (USY-8). The silica/alumina molar ratio of USY-8 was 82.2. Alkylation reaction was conducted by the same manner as that of Example 5 except that USY-8 was used in place of USY-1 and decalin (weight ratio of decalin/isopropylnaphthlene=½) was supplied to the bed. The results are shown in Table 2 and FIG. 2.

EXAMPLE 11

Alkylation reaction was conducted by the same manner as that of Example 5 except that USY-4 prepared in Example 4 was used in place of USY-1 used in Example 5. The results are shown in Table 2 and FIG. 2.

EXAMPLE 12

Dealumination and alkylation reaction was conducted by the same manner as that of Example 5 except that the dealumination was conducted by using 1.60 mol/l of an aqueous trifluoromethanesulfonic acid solution to obtain a catalyst (USY-9). The silica/alumina molar ratio of USY-9 was 318. The results are shown in Table 2 and FIG. 2.

COMPARATIVE EXAMPLE 3

Alkylation reaction was conducted by the same manner as that of Example 5 except that an untreated ultrastable Y zeolite (manufactured and sold by TOSOH Co. Ltd., TSZ-330HUA) was used in place of USY-1 as the catalyst. The results are shown in Table 2 and FIG. 2. Deactivation of the catalyst was remarkable.

TABLE 2

|  | Example 5 | Example 6 | Example 7 | Example 8 | Example 9 | Example 10 | Example 11 | Example 12 | Comparative example 3 |
|---|---|---|---|---|---|---|---|---|---|
| Reaction conditions |  |  |  |  |  |  |  |  |  |
| Catalyst | USY-1 | USY-6 | USY-7 | USY-2 | USY-3 | USY-8 | USY-4 | USY-9 | TSZ-330 |
| SiO₂/Al₂O₃ | 20.6 | 14.9 | 19.5 | 22.9 | 63.3 | 82.2 | 100 | 318 | 5.9 |
| Temperature (°C.) | 220 | 220 | 220 | 220 | 220 | 220 | 220 | 220 | 220 |
| Pressure (kg/cm² G) | 4.0 | 4.0 | 4.0 | 4.0 | 4.0 | 4.0 | 4.0 | 4.0 | 4.0 |
| H.C | decalin | decalin | decalin | decalin | decalin | decalin | decalin | decalin | decalin |

TABLE 2-continued

| | Example 5 | | Example 6 | | Example 7 | | Example 8 | | Example 9 | | Example 10 | | Example 11 | | Example 12 | | Comparative example 3 | |
|---|---|---|---|---|---|---|---|---|---|---|---|---|---|---|---|---|---|---|
| H.C./IPN (Weight ratio) | 1.0 | | 1.0 | | 1.0 | | 1.0 | | 1.0 | | 0.5 | | 1.0 | | 1.0 | | 1.0 | |
| Results | | | | | | | | | | | | | | | | | | |
| Reaction time (Hr) | 1 | 16 | 1 | 10 | 1 | 116 | 1 | 20 | 1 | 10 | 1 | 18 | 1 | 20 | 1 | 6 | 1 | 10 |
| IPN Percent conversion (%) | 74.9 | 70.4 | 59.8 | 54.7 | 64.3 | 50.8 | 74.3 | 70.9 | 71.5 | 72.4 | 71.8 | 66.9 | 70.2 | 66.7 | 51.9 | 42.9 | 58.1 | 31.6 |
| NL Selectivity (%) | 3.9 | 4.3 | 13.8 | 12.6 | 10.9 | 7.0 | 4.7 | 4.3 | 4.9 | 5.6 | 6.4 | 8.6 | 7.1 | 6.2 | 4.8 | 5.6 | 9.1 | 15.9 |
| DIPN Selectivity (%) | 68.5 | 66.3 | 69.6 | 69.4 | 66.1 | 71.6 | 70.4 | 67.8 | 59.9 | 60.7 | 69.4 | 70.8 | 59.3 | 62.7 | 59.2 | 64.2 | 80.2 | 77.9 |
| TIPN Selectivity (%) | 27.6 | 29.4 | 16.6 | 18.0 | 23.0 | 21.4 | 24.9 | 27.8 | 33.1 | 30.3 | 24.2 | 20.6 | 33.7 | 31.1 | 36.0 | 30.1 | 10.7 | 6.2 |
| DIPN isomers (%) | | | | | | | | | | | | | | | | | | |
| 2,6-DIPN | 40.8 | 39.3 | 40.3 | 37.0 | 40.4 | 35.2 | 40.3 | 39.7 | 40.8 | 40.3 | 40.8 | 40.5 | 39.7 | 39.8 | 39.5 | 36.6 | 38.4 | 34.9 |
| 2,7-DIPN | 40.8 | 37.6 | 42.2 | 39.7 | 42.3 | 32.4 | 40.3 | 36.7 | 40.5 | 39.6 | 40.5 | 39.4 | 39.2 | 35.7 | 30.3 | 26.4 | 42.4 | 37.8 |
| $10^2 \beta$ (h$^{-1}$) | 0.56 | | 0.92 | | 0.21 | | 0.18 | | 0.0 | | 0.41 | | 0.46 | | 3.0 | | 7.2 | |

Remarks:
NL: naphthalene.
IPN: isopropylnaphthalene.
DIPN: diisopropylnaphthalene.
TIPN: tri or tetraisopropylnaphthalene
H.C.: saturated polycarbocyclic compound
(1) IPN percent conversion: 100-IPN concentration (mol %) in products
(2) NL selectivity: [NL concentration (mol %) in products/IPN percent conversion (mol %)] × 100
(3) DIPN selectivity: [DIPN concentration (mol %) in products/IPN percent conversion (mol %)] × 100
(4) TIPN selectivity: [TIPN concentration (mol %) in products/IPN percent conversion (mol %)] × 100
(5) DIPN isomers: Concentration of 2,6- or 2,7-isomer in products of diisopropylnaphthalene isomers

EXAMPLE 13

Naphthalene was used as starting materials. Alkylation reaction was conducted in the same manner as that of Example 5 except that 10 g/Hr of a naphthalene in decalin solution (decalin/naphthalene (weight ratio)=5/1), propylene (propylene/naphthalene (molar ratio)=3/4) and hydrogen (hydrogen/naphthalene (molar ratio)=4/1) were supplied to a catalyst bed.

Results are shown in Table 3.

EXAMPLES 14 and 15

Alkylation reactions were conducted by the same manner as that of Example 13 except that USY-6 prepared in Example 6 (Example 14) or USY-2 prepared in Example 2 (Example 15) were used in place of USY-1 used in Example 13. The results are shown in Table 3.

COMPARATIVE EXAMPLE 4

Alkylation reaction was conducted by the same manner as that of Example 13 except that an untreated ultrastable Y zeolite (manufactured and sold by TOSOH Co. Ltd., TSZ-330HUA) was used in place of USY-1 as the catalyst. The results are shown in Table 3.

TABLE 3

| | Example 13 | | Example 14 | | Example 15 | | Comparative Example 4 | |
|---|---|---|---|---|---|---|---|---|
| Reaction Conditions | | | | | | | | |
| Catalyst | USY-1 | | USY-6 | | USY-2 | | TSZ-330 | |
| SiO$_2$/Al$_2$O$_3$ | 20.6 | | 14.9 | | 22.9 | | 5.9 | |
| Temperature (°C.) | 220 | | 220 | | 220 | | 220 | |
| Pressure (kg/cm$^2$ G) | 4.0 | | 4.0 | | 4.0 | | 4.0 | |
| H.C. | decalin | | decalin | | decalin | | decalin | |
| H.C./IPN (Weight ratio) | 5.0 | | 5.0 | | 5.0 | | 5.0 | |
| Results | | | | | | | | |
| Reaction time (Hr) | 1 | 8 | 1 | 8 | 1 | 8 | 1 | 8 |
| NL percent conversion (%) | 47.3 | 52.3 | 49.6 | 43.5 | 52.8 | 55.7 | 46.1 | 39.1 |
| IPN selectivity (%) | 68.0 | 71.4 | 73.0 | 74.8 | 69.2 | 67.5 | 77.9 | 79.3 |
| DIPN selectivity (%) | 29.4 | 26.5 | 25.8 | 23.9 | 28.1 | 29.5 | 21.5 | 19.9 |
| TIPN selectivity (%) | 2.6 | 2.1 | 1.3 | 1.4 | 2.6 | 3.0 | 0.6 | 0.8 |
| IPN isomers (%) $\beta$ - IPN | 93.5 | 92.8 | 93.1 | 91.4 | 93.5 | 93.3 | 92.6 | 87.8 |

Remarks:
NL: naphthalene.
IPN: isopropylnaphthalene.
DIPN: diisopropylnaphthalene.
TIPN: tri or tetraisopropylnaphthalene
H.C.: saturated polycarbocyclic compound
(1) NL percent conversion: 100 - naphthalene concentration (mol %) in products
(2) IPN selectivity: [IPN concentration (mol %) in products/NL percent conversion (mol %)] × 100
(3) DIPN selectivity: [DIPN concentration (mol %) in products/NL percent conversion (mol %)] × 100
(4) TIPN selectivity: [TIPN concentration (mol %) in products/NL percent conversion (mol %)] × 100
(5) DIPN isomers: Concentration of $\beta$ - isomer in IPN isomers containing products

What is claimed is:

1. A method for preparation of mono and/or diisopropylnaphthalenes comprising reacting naphthalene and/or monoisopropylnaphthalene with propylene, in the presence of at least one saturated polycarbocyclic compound and a catalyst comprising a Y zeolite having the silica/alumina molar ratio of from 10 to 350.

2. A method of claim 1 wherein the silica/alumina molar ratio ranges from 20 to 100.

3. A method of claim 1 wherein the reaction is carried out at 160° to 300° C.

4. A method of claim 1 wherein the reaction is carried out under pressure of 0.5 kg/cm² or more.

5. A method of claim 1 wherein the saturated polycarbocyclic compound(s) is used int he range of from 0.05 to 10 (weight ratio on the basis of the weight of naphthalene and/or monoisopropylnaphthalene).

6. A method of claim 1 wherein the saturated polycarbocyclic compound is selected from the group consisting of polycarbocyclic compounds with separate ring-systems, polycarbocyclic compounds with combined ring-systems, polycarbocyclic compounds with fused ring-systems and polycarbocyclic compounds with bridged ring-systems.

7. A method of claim 1 wherein the saturated polycarbocyclic compound is selected from the group consisting of bicyclopropyl, bicyclopentyl, bicyclohexyl, cyclopentylcyclohexane, spiro[2,2]heptane, spiro[2,3]hexane, spiro[2,4]heptane, spiro[3,3]heptane, spiro[3,4]octane, bicyclo[4,2,0]octanehydroindane, decalin, perhydrophenanthroline, perhydroanthracene, norpinane, norbornane and bicyclo[2,2,1]octane.

8. A method of claim 6 the saturated polycarbocyclic compound is polycarbocyclic compounds with fused ring-systems or polycarbocyclic compounds with separate ring-systems.

9. A method of claim 7 wherein the saturated polycarbocyclic compound is decalin or bicyclohexyl.

10. A method for preparation of diisopropylnaphthalenes comprising reacting monoisopropylnaphthalene with propylene in the presence of a catalyst comprising a Y zeolite wherein the silica/alumina molar ratio ranges from 15 to 110.

11. A method of claim 10, wherein the silica/alumina molar ratio ranges from 20 to 80.

12. A method of claim 10, wherein the Y zeolite is an ultrastable Y zeolite.

13. A method of claim 10 wherein the reaction is carried out at 160° to 300° C.

14. A method of claim 10 wherein the reaction is carried out by controlling the weight hourly space velocity (WHSV) within 0.2 to 50 $Hr^{-1}$.

* * * * *